US010835117B2

(12) United States Patent
Mantysalo et al.

(10) Patent No.: US 10,835,117 B2
(45) Date of Patent: *Nov. 17, 2020

(54) TESTING AND DETERMINING A THRESHOLD VALUE

(71) Applicant: Ocuspecto Oy, Turku (FI)

(72) Inventors: Tapio Mantysalo, Hevonpaa (FI); Markku Leinonen, Turku (FI); Harri Kaasalainen, Turku (FI); Katariina Sampinen, Hajala (FI); Marika Ojala, Rusko (FI)

(73) Assignee: Ocuspecto Oy, Turku (FI)

( * ) Notice: Subject to any disclaimer, the term of this patent is extended or adjusted under 35 U.S.C. 154(b) by 109 days.

This patent is subject to a terminal disclaimer.

(21) Appl. No.: 16/042,810

(22) Filed: Jul. 23, 2018

(65) Prior Publication Data

US 2018/0368677 A1     Dec. 27, 2018

Related U.S. Application Data

(63) Continuation of application No. 14/915,640, filed as application No. PCT/FI2014/050671 on Sep. 2, 2014, now Pat. No. 10,736,502.

(30) Foreign Application Priority Data

Sep. 2, 2013  (FI) .................................... 20135885

(51) Int. Cl.
*A61B 3/02*    (2006.01)
*A61B 3/024*   (2006.01)
(Continued)

(52) U.S. Cl.
CPC ............ *A61B 3/024* (2013.01); *A61B 3/0033* (2013.01); *A61B 3/0091* (2013.01); *A61B 3/022* (2013.01);
(Continued)

(58) Field of Classification Search
CPC ....... A61B 3/024; A61B 3/0091; A61B 3/032; A61B 3/113; A61B 3/0008; A61B 3/0033;
(Continued)

(56) References Cited

U.S. PATENT DOCUMENTS 2,283,752 A    5/1942  Gonsett
4,559,047 A   12/1985  Kapralis et al.
(Continued)

FOREIGN PATENT DOCUMENTS

CN         1438852 A      8/2003
CN    201480060873.X      4/2018
(Continued)

OTHER PUBLICATIONS

Partial Translation of Official Action in Japanese application 2016-539602.
(Continued)

*Primary Examiner* — Mahidere S Sahle
(74) *Attorney, Agent, or Firm* — James C. Lydon

(57) ABSTRACT

This invention relates to testing and determining a threshold value used in psychometric testing in field of ophthalmology, neuro-ophthalmology and visual neuropsychology. The method comprises at least the following steps:

a) displaying a symbol with a distinctive visual appearance and with a stimulus level to a display at a stimulus time-point, the symbol selected from a group of possible symbols, b) monitoring if a response is given on a response device with multiple choices, each choice representing a possible visual appearance or location of the symbol, and b1) if a response is not given in a response time-limit from the stimulus time-point, increasing the stimulus level of the symbol by a predetermined step and returning to step a), or (Continued)

b2) if a response is given in the response time-limit from the stimulus time-point, comparing the response to symbol displayed in step a), and c1) if the response does not correspond to the symbol displayed in step a), producing, e.g. displaying, an error feedback and returning to step a), or c2) if the response corresponds to the symbol displayed in step a), determining if stop criteria for the test is satisfied, and d1) if stop criteria for the test is not satisfied, decreasing the stimulus level by a predetermined step and returning to step a), or d2) if stop criteria for the test is satisfied, ending the test.

8 Claims, 9 Drawing Sheets

(51) Int. Cl.
| | |
|---|---|
| A61B 5/16 | (2006.01) |
| A61B 3/00 | (2006.01) |
| A61B 3/028 | (2006.01) |
| A61B 3/032 | (2006.01) |
| A61B 3/06 | (2006.01) |
| A61B 5/00 | (2006.01) |
| A61B 3/18 | (2006.01) |
| H04N 5/58 | (2006.01) |

(52) U.S. Cl.
CPC .............. *A61B 3/028* (2013.01); *A61B 3/032* (2013.01); *A61B 3/063* (2013.01); *A61B 3/066* (2013.01); *A61B 3/18* (2013.01); *A61B 5/163* (2017.08); *A61B 5/7445* (2013.01); *H04N 5/58* (2013.01)

(58) Field of Classification Search
CPC ......... A61B 3/02; A61B 3/028; A61B 3/0285; A61B 3/063; A61B 3/08; A61B 5/16
USPC ................ 351/203, 205, 211, 212, 221–226, 351/237–244, 246
See application file for complete search history.

(56) References Cited

U.S. PATENT DOCUMENTS

| | | | |
|---|---|---|---|
| 4,679,920 A | 7/1987 | Takashi et al. | |
| 4,869,589 A | 9/1989 | Blair et al. | |
| 4,907,580 A | 3/1990 | Leonardi | |
| D309,465 S | 7/1990 | Russell | |
| 5,035,500 A | 7/1991 | Rorabaugh et al. | |
| 5,183,059 A | 2/1993 | Leonardi | |
| 5,422,690 A | 6/1995 | Rothberg et al. | |
| 5,459,536 A | 10/1995 | Shalon et al. | |
| 5,565,949 A | 10/1996 | Kasha, Jr. | |
| 5,592,247 A | 1/1997 | Trokel | |
| 5,740,550 A | 4/1998 | Yavitz | |
| 5,769,806 A | 6/1998 | Radow | |
| 5,825,460 A | 10/1998 | Kohayakawa | |
| 5,920,375 A | 7/1999 | Fahle et al. | |
| D421,124 S | 2/2000 | Yavitz | |
| D424,691 S | 5/2000 | Yavitz | |
| D425,623 S | 5/2000 | Funk | |
| D436,665 S | 1/2001 | Becker | |
| D440,660 S | 4/2001 | Sternberg | |
| D442,693 S | 5/2001 | Sternberg et al. | |
| D444,236 S | 6/2001 | Koop et al. | |
| 6,612,700 B2 | 9/2003 | Walther | |
| 6,817,715 B2 | 11/2004 | Leinonen | |
| D533,572 S | 12/2006 | Howard et al. | |
| 7,265,917 B2 | 9/2007 | Kugler et al. | |
| D552,736 S | 10/2007 | Yamaoka | |
| 7,478,911 B2 | 1/2009 | Inakagata et al. | |
| D607,562 S | 1/2010 | Heine et al. | |
| D614,774 S | 4/2010 | Gausmann et al. | |
| D639,441 S | 6/2011 | Sferle | |
| 8,038,297 B1 | 10/2011 | Hofeldt | |
| D674,903 S | 1/2013 | Harder | |
| D698,444 S | 1/2014 | Mensink | |
| 8,691,193 B2 | 4/2014 | Rodriguez et al. | |
| D705,430 S | 5/2014 | Sekine | |
| D709,199 S | 7/2014 | Kambe et al. | |
| D723,698 S | 3/2015 | Cockley | |
| D734,471 S | 7/2015 | Pollanen | |
| 2004/0105073 A1 | 6/2004 | Maddalena et al. | |
| 2005/0068498 A1 | 3/2005 | Suzuki | |
| 2005/0128434 A1 | 6/2005 | Ianchulev et al. | |
| 2006/0001831 A1 | 1/2006 | Sumiya | |
| 2006/0087618 A1 | 4/2006 | Smart et al. | |
| 2006/0114414 A1 | 6/2006 | McGrath et al. | |
| 2007/0182928 A1 | 8/2007 | Sabel | |
| 2008/0024724 A1 | 1/2008 | Todd | |
| 2008/0212032 A1 | 9/2008 | Seiller et al. | |
| 2009/0051877 A1* | 2/2009 | Delahunt ............... G09B 7/04 351/246 |
| 2009/0303626 A1 | 12/2009 | Xalter et al. | |
| 2010/0128222 A1 | 5/2010 | Donaldson | |
| 2010/0171926 A1 | 7/2010 | Padula | |
| 2010/0208254 A1 | 8/2010 | Amz | |
| 2012/0081669 A1 | 4/2012 | Feiertag et al. | |
| 2012/0092620 A1 | 4/2012 | Epitropoulos | |
| 2014/0340642 A1 | 11/2014 | You et al. | |
| 2014/0362346 A1 | 12/2014 | Leinonen et al. | |

FOREIGN PATENT DOCUMENTS

| | | |
|---|---|---|
| EP | 2561799 | 2/2013 |
| GB | 2397391 | 7/2004 |
| JP | H024309 A | 1/1990 |
| JP | 07299033 A | 11/1995 |
| JP | 0880281 A | 3/1996 |
| JP | H0866360 A | 3/1996 |
| JP | 2000310983 A | 11/2000 |
| JP | 2002209849 A | 7/2002 |
| JP | 2003088501 A | 3/2003 |
| JP | 200393344 | 4/2003 |
| JP | 2004317530 A | 11/2004 |
| JP | 2005256860 A | 9/2005 |
| JP | 2005296402 A | 10/2005 |
| JP | 200614766 | 1/2006 |
| JP | 2006267225 A | 10/2006 |
| JP | 2006304811 A | 11/2006 |
| JP | 2007277239 A | 10/2007 |
| JP | 2011139914 A | 7/2011 |
| JP | 2016539603 | 5/2018 |
| WO | 02/00105 A1 | 1/2002 |
| WO | 2005093679 | 10/2005 |
| WO | 2008005848 | 1/2008 |
| WO | 2008078106 | 7/2008 |
| WO | 2013094995 | 6/2013 |
| WO | 2013096473 A1 | 6/2013 |
| WO | 2013120075 A1 | 8/2013 |
| WO | 2015023676 | 2/2015 |

OTHER PUBLICATIONS

Bodrogi et al., "Spectral Sensitivity and Additivity of Discomfort Glare Under Street and Automotive Lighting Conditions," 20 Light & Engineering 66-71 (2012).

Charoensap et al., "Evaluation of Discomfort Glare From Color LEDs Under Different Illuminance," Proceedings of the 1st Asia Color Association Conference (ACA2013) Paper OA31 Thanyaburi: Blooming Color for Life 62 (Dec. 11-14, 2013).

Fekete et al., "Spectral Discomfort Glare Sensitivity Investigations," 30 Ophthal. Physiol. Opt. 182 (2010).

Kotani et al., "Visual Field Screening System by Using Overlapped Fixation Patterns," 95 Electronics and Communications in Japan 29 (2012).

(56) References Cited

OTHER PUBLICATIONS

Namiki et al., "Measurement of Glare Disability Using an Automated Perimeter," 18 J. Cataract Refract. Surg. 391 (1992).
Niedling et al., "Influence of a Glare Sources Spectrum on Discomfort and Disability Glare Under Mesopic Conditions," Proceedings of CIE Centenary Conference Towards a New Century of Light 340 (2013).
Ryckaert et al., "Linear LED Tubes versus Fluorescent Lamps: An Evaluation," 49 Energy and Buildings 429 (2012).
Sivak et al., "Blue Content of LED Headlamps and Discomfort Glare," Report No. UMTRI-2005-2 (Univ. Mich. 2005).
Zhang et al., "Effect of the Correlated Color Temperature of Light on Overhead Glare in Offices," 44 Proceedings of the SID Symposium Digest of Technical Papers 1096 (2013).
Zydek et al., "A New Concept of Disability Glare Under Traffic Lighting Conditions: Experimental Setup, Results and Analysis of Spectral Sensitivity," 14 Proceedings of the 9th International Symposium on Automotive Lighting 362 (2011).

\* cited by examiner

TESTING AND DETERMINING A THRESHOLD VALUE

TECHNICAL FIELD OF THE INVENTION

The invention relates to critical stimulus level or critical symbol size testing, i.e. a method for testing and determining a threshold value in psychometric testing in field of ophthalmology, neuro-ophthalmology and visual neuropsychology, for example in testing of visual acuity, contrast sensitivity, color vision deficiency or sensitivity to disability glare of a person.

TECHNICAL BACKGROUND

Testing of visual acuity, contrast sensitivity and sensitivity to disability glare have traditionally needed assistance from test personnel and manual interpretation of the test subject's answers and manual reporting. While automating the test procedure it is important that the tests are reliable, fast and that they won't require continuous assistance or manual reporting work from test personnel.

Most common psychometric tests are different multiple-alternative forced-choice methods. In these a person has to identify a symbol of variable size, contrast or color visible on the display unit with or without glare light. The problem with these methods is that in order to compensate for the differences between aggressively guessing test subject and cautious test subject, the test subject is forced to guess even when the symbol is not seen. Therefore, test subject can very often correctly guess the symbol even without seeing it correctly. To decrease the effects of guessing more alternatives and more test steps are required for a reliable estimation of the threshold of vision. Increasing the amount of alternatives makes the test more demanding to operate for the test subject and stressful for the test subject.

E.g. in the Freiburg Visual Acuity test variable size or contrast Landolt C or tumbling E symbols (optotypes) are presented on a monitor in one of several orientations: This is adjustable, but eight orientations are referred to in the literature to be needed for repeatable results. The person presses one of eight buttons which are arranged according to the eight possible positions of the symbols. To estimate the acuity threshold the responses on the buttons are recorded and a mathematical model determines the result. The patient should guess the symbol direction if she/he is not sure of it. Measurement terminates after a fixed number of trials, or after a number of threshold crossing, or after another criteria.

U.S. Pat. No. 4,861,156 describes a visual acuity test procedure using a video capable of presenting and projecting means and a control unit. GB 2,397,391 discloses a visual acuity computerized test utilizing a remote control unit. WO 2008081446 A2 describes a method, algorithm and device for testing visual acuity. In US 2004/105073 a threshold value in testing of visual acuity is determined.

OBJECT OF THE INVENTION

It is an object of the present invention to reduce or even eliminate the above-mentioned problems appearing in prior art.

It is an object of the present invention to provide for an effective, easy and reliable two-alternative time-limited choice method for testing and determining a threshold value in psychometric tests in the field of ophthalmology, neuro-ophthalmology and visual neuropsychology, and especially to test visual acuity, contrast sensitivity, color vision deficiency and separation and sensitivity to disability glare tests.

It is an object of the present invention to provide psychometric testing in the field of ophthalmology, neuro-ophthalmology and visual neuropsychology, and especially to test visual acuity, contrast sensitivity, color vision deficiency and sensitivity to disability glare of a person wherein said method comprises evaluating the ability of the person to identify a symbol, pattern or an optotype visible on a display said identifying comprising recognition of said symbol and/or its orientation.

The symbol, i.e. optotype, can be a complex pattern, e.g. if task is to identify on which side of the display area there is a first symbol compared to a second symbol (Where is the cat, as compared to the dog, for example. The symbol can also be a very simple pattern, e.g. task could be to identify on which side of the display area there is a dot, ring or stripes as compared any of these or other disturbing pattern or blank. Most commonly the task is to recognize traditional ophthalmic optotypes (e.g. Landolt C, tumbling E, Lea Numbers or Lea Symbols) from each other or to detect orientation of the these optotypes. In order to be short, the term 'symbol' is used in this text to represent all of these patterns, figures and optotypes and their derivatives.

SUMMARY OF THE INVENTION

Among others, in order to realize the objects mentioned above, method and apparatus and other objects according to the invention are characterized by what is presented in the characterizing parts of the enclosed independent claims.

The embodiments, examples and advantages mentioned in this text relate, where applicable, to methods as well as to any apparatuses or uses according to the invention, even though it is not always specifically mentioned.

A typical method for testing and determining a threshold value is used in psychometric testing in field of ophthalmology, neuro-ophthalmology and visual neuropsychology. For example the invention can be used in testing of visual acuity, contrast sensitivity, color vision deficiency or sensitivity to disability glare of a person. A typical method comprises at least the following steps:
a) displaying a symbol with a distinctive visual appearance and with a stimulus level to a display at a stimulus time-point, the symbol selected from a group of possible symbols,
b) monitoring if a response is given on a response device with multiple choices, each choice representing a possible visual appearance or location of the symbol, and
b1) if a response is not given in a response time-limit from the stimulus time-point, increasing the stimulus level of the symbol by a predetermined step and returning to step a), or
b2) if a response is given in the response time-limit from the stimulus time-point, comparing the response to symbol displayed in step a), and
c1) if the response does not correspond to the symbol displayed in step a), producing, e.g. displaying, an error feedback and returning to step a), or
c2) if the response corresponds to the symbol displayed in step a), determining if stop criteria for the test is satisfied, and
d1) if stop criteria for the test is not satisfied, decreasing the stimulus level by a predetermined step and returning to step a), or
d2) if stop criteria for the test is satisfied, ending the test.

A typical apparatus for testing and determining a threshold value in psychometric testing in field of ophthalmology, neuro-ophthalmology and visual neuropsychology, e.g. visual acuity, contrast sensitivity, color vision deficiency or sensitivity to disability glare comprises:

- a display for displaying a symbol,
- a response device with multiple choices, each choice representing a possible visual appearance or location of the symbol,
- a computer with a computer program product encoding a computer program of instructions for executing a computer process for the method of the invention.

Threshold value, i.e. the critical stimulus level may be obtained as the smallest stimulus level for which in step c2) the response corresponded to the symbol displayed in step a) or it may be the last threshold crossing value, or obtained by statistical calculation on the number of different symbol sizes of correct and incorrect responses, or by a calculation based on threshold crossings, or by some other calculation.

Critical stimulus level, such as critical symbol size is an important indication of an individual's performance in relation to certain daily activities such as driving, reading, and video display terminal works. When the person is using extended time, i.e. reaction time for identification of the symbol is longer than at critical stimulus level, he/she can identify even smaller symbols or symbols with lower contrast than the critical stimulus level. The lowest stimulus level, e.g. smallest symbol size, which can be identified using extended time is called the 'threshold level' or threshold size. This is used for calculating visual acuity or contrast sensitivity. The difference between critical stimulus level and threshold level (e.g. symbol sizes for critical symbol size and threshold size) varies for various conditions of visual system. E.g. the enlargement of the critical symbol size can be an indication of ocular disease e.g. ocular surface disease i.e. dry eye, mild cataract or posterior capsule opacification after cataract surgery, epiretinal membranes of macular area of fundus of the eye even if the threshold value of the visual acuity or contrast sensitivity is in the normal range. Testing for the mentioned indications are some applications the present invention can be used for.

The term "contrast" is the difference in luminance and/or color of the foreground and background of the object that makes an object, or its representation in an image or display, distinguishable.

The term "contrast sensitivity" is a measure of the ability of the visual system to detect contrast.

In an embodiment the reaction time starting from the appearance of the symbol to be identified on the display panel to the correct response is recorded. The smallest symbol size which doesn't cause prolongation of the reaction time, when continually reducing the size of symbols to be identified, is named as 'critical symbol size'.

In one embodiment the method uses a so-called staircase procedure, which starts with a symbol of high intensity or high stimulus level that is easy to detect. The stimulus level is then decreased by a defined amount until the test subject does not see the symbol, at which point the staircase is reversed and stimulus level is increased by a defined amount until the test object responds correctly—then another reversal is triggered. At each reversal, the defined amount of increasing or decreasing the stimulus level may be changed. This kind of reversal is also a threshold crossing.

A typical staircase pattern of decreasing the stimulus level is 5, 3, 2, 1, 1, where each number represents a relative stimulus level increase/decrease amount after reversal, '5' being the first used.

In an embodiment of the invention the stop criteria of the test is satisfied when either a pre-defined number of test steps is achieved, or a pre-defined number of threshold crossings is achieved, or a pre-defined amount of responses (or non-responses) of stimulus intensity bin or bins are achieved. There can also be other end criteria for the test, such as time limit, or achieving a pre-defined statistical reliability index.

The invention provides a very fast test, because of the relatively short time-limitation when showing the symbol, such as an optotype, pattern or task. This allows also making the test several times in a row, to estimate the reliability of the test and also to get more accurate and/or repeatable results. From running the test several times, or for prolonged period, it is possible to calculate the reliability of the overall test.

The invention provides a test, where the test subject is not forced to make a choice. No error message is needed if a response is not given in a response time-limit. Test subject may simply wait until he/she sees the symbol, e.g. optotype, pattern or task. Many patients, especially if cautious by nature, find it frustrating when they are forced to guess, and therefore the method according to the invention is better received by this kind of patients, causing less mental stress in the testing situation and therefore yielding to more repeatable results.

The invention provides a test, where the user is discouraged from guessing by giving clear feedback on wrong answers. In case of a wrong answer, typically a symbol with same stimulus level is displayed again after the feedback. In some embodiments, a symbol with another stimulus level may also be used after the error. Typically a wrong answer by the patient is not interpreted as 'symbol not identified' by the algorithm of the invention. The error feedback may comprise e.g. a visual message, an audible error sound or a vibration message.

Having a relatively short timeout before increasing the stimulus level makes waiting natural in cases where the symbol, such as an optotype, pattern or task is not seen.

In an embodiment the response time-limit is more than 0.5 seconds but less than 3 seconds. The response time-limit may be selected to be as needed, e.g. 0.5-3 seconds, 0.5-4 seconds, 0.5-2 seconds, 1-4 seconds, 1-3 seconds, less than 5 seconds, less than 4 seconds, less than 3 seconds. Short time-out before deciding that the stimulus level was too low, e.g. a symbol was too small, makes the test fast. The test also becomes more repeatable, because the test subject does not have time to develop methods to compensate lack of vision with brain functions, which will vary considerably over time.

In an embodiment the group of possible symbols comprises only two possible symbols, e.g. a symbol indicating left and a symbol indicating right or up and down symbols. Using only two possibilities makes the test easier and less stressful for the test subject.

In an embodiment the response device comprises only two possible choice actuators, i.e. means to report a choice, such as buttons. E.g. two keys on a normal computer keyboard may be used, e.g. left and right or up and down arrows. Using only two possibilities, i.e. buttons, allows a simple and reliable response device and programming. Pressing of the correct button on the response device indicates a correct identification of the symbol.

In an embodiment the response device is a remote controller or a portable communication device, such as a portable phone or a tablet computer. The buttons may be e.g. physical pressable buttons, joystick or electric images on a touch-screen or response device may function with voice feedback.

In an embodiment, e.g. when testing visual acuity or low contrast visual acuity, the stimulus level of the symbol is the size of the symbol. In this case increasing or decreasing the stimulus level of the symbol means increasing or decreasing the size of the symbol displayed.

In an embodiment, e.g. when testing contrast sensitivity the stimulus level of the symbol is the relative visual contrast level of the symbol on the display. In this case increasing or decreasing the stimulus level of the symbol means increasing or decreasing the contrast level of the symbol displayed.

In an embodiment, e.g. when testing color vision deficiency, the stimulus level of the symbol is the relative color difference of the symbol on the display. In this case increasing or decreasing the stimulus level of the symbol means increasing or decreasing the color difference of the symbol displayed.

In an embodiment the displayed symbol is adjustable in one or more of size, contrast, color and pattern, compared to the background where it is displayed or figure/pattern of comparison.

In an embodiment of the invention
if the response is not given in a response time-limit and the previous response corresponded to the displayed symbol, or
if the response corresponds to the symbol displayed and the previous response was not given in a response time-limit, then the predetermined step by which the stimulus level of the symbol is changed is decreased, e.g. to half of its previous value.

In an embodiment of the invention the end criteria may vary according to the selected test stepping algorithm and desired level of reliability and/or amount of data. The stepping algorithm may be for example a staircase method, ZEST (zippy estimation by sequential testing), PEST (parameter estimation by sequential testing), Best-PEST (improved PEST), QUEST, Bayesian adaptive psychometric method, etc.

In an embodiment if for a number of times in a row, e.g. 2, 3, 4 or 5 adjacent times,
the response is not given in the response time-limit from the stimulus time-point, or
the response corresponds to the symbol displayed in step a), then the predetermined amount by which the stimulus level of the symbols are changed is increased, e.g. to double of its previous value or some other value, because it can be considered that the algorithm is not near the threshold level, and the threshold level can be reached faster if the amount of changing the stimulus level is increased.

In an embodiment two or more test rounds are performed for each test subject. Based on deviation in the results of the test rounds, optionally more test rounds can be made. The latter test rounds may have fewer steps than the first one and can be started with a stimulus level close to the result of the previous round, i.e. close to the then estimated threshold value in order to reduce total test steps needed and therefore total test time.

Reliability of the measurement can be estimated e.g. with the following indicators: Differences of results between the test rounds gives indication of repeatability of the test or indication of patient concentration. Amount of wrong answers compared to symbols shown, i.e. steps used, gives an indication of how much the patient guesses. If the amount of changing the stimulus level needs to be increased, this can be used as an indication that the patient is not maybe concentrating on the task properly, or has misunderstood the task.

One aspect of the invention is a computer program product encoding a computer program of instructions for executing a computer process according to the method of the invention.

One aspect of the invention is a computer program distribution medium readable by a computer and encoding a computer program of instructions for executing a computer process according to the method of the invention.

In one embodiment the invention is used with a stand-alone medical device for testing a patient, which comprises in one-piece configuration:
a first testing device comprising a perimeter surface having a first side to be viewed by the patient during testing and second side (4) not to be seen by the patient during testing,
one or more second testing devices from the group of:
a) a visual acuity measurement device to be viewed by the patient during testing of visual acuity,
b) a contrast sensitivity testing device to be viewed by the patient during testing of contrast sensitivity,
c) a glare disability testing device to be viewed by the patient during testing of glare,
d) a color vision deficiency testing device to be viewed by the patient during testing of color vision deficiency,
user interface device for controlling the use of the first and second testing devices.

This stand-alone medical device may be used in a method for testing a patient with a stand-alone medical device in one-piece configuration described later in this text. This stand-alone medical device may also be used without the present two-alternative time-limited choice method for testing and determining a threshold value invention and/or in combination with some other embodiment or feature mentioned in this text. This stand-alone medical device can measure some or most, if not all of the following functional abilities of a person being tested: functioning of the visual system, vision, attention, perceptual skills, memory, decision making, and reaction time. This stand-alone medical device can assess various aspects of function of the visual system, such as visual field, visual search ability, visual decision making, saccadic eye movement, visual acuity, contrast sensitivity, sensitivity to glare and spatial short term memory. It may provide for a reliable and easy-to-use method and device to test whether a person fulfills driver requirements for safe driving.

Some differences between some embodiments of the present invention and traditional measurement algorithms are listed in Table 1:

TABLE 1

| Case | Traditional method | New method |
| --- | --- | --- |
| Patient reports the symbol correctly | Conclusion: The patient saw the symbol.<br>Indication to patient:<br>New figure (often more difficult to see) is presented. | Conclusion: the patient saw the symbol.<br>Indication to patient:<br>New figure (often more difficult to see) is presented. |
| Patient reports the symbol incorrectly | Conclusion: The patient did not see the symbol.<br>Indication to patient:<br>New symbol (often easier to see) is presented<br>Comment:<br>The patient is not indicated the error, so that he/she would not be afraid of guessing. The patient is in fact encouraged to guess if he/she does not see. | No conclusion.<br>Indication to patient:<br>Visible and/or audible Error sign first. Then new symbol will be presented, preferably, but not necessary of the same size.<br>Novelty:<br>The patient will be shown that he/she made an error, thus encouraging him/her not to guess. |

TABLE 1-continued

| Case | Traditional method | New method |
| --- | --- | --- |
| Patient reports the symbol correctly, but slowly (later than time-limit) | Conclusion: The patient did not see the symbol. Indication to the patient: New symbol (often easier to see) is presented. Comment: The patient is given rather long time to react, typically at least 5 seconds up to infinity. The patient has time to think and develop methods to compensate poor vision with brain functions. | Conclusion: The patient did not see the symbol. Indication to the patient: New symbol (easier to see) is presented. Comment: The timeout value is typically 2-3 seconds only. Short timeout encourages the patient to wait until he/she sees the figure, rather than guessing. |
| Instructions to the patient | Take your time to look at the symbol. If you cannot recognize it, guess. | Report the symbol as quickly as you can see it. If you cannot see the symbol, wait a little while until you see it. |
| Amount of different symbols (i.e. optotypes) | Min. 3, typically 4, and for truly repeatable measurements 8 or more different symbols are needed. The reporting using a keyboard or another input device may be difficult to the user due to the amount of different choices. The user must often look at the response device before selecting the response. | 2 different symbols. The reporting using a keyboard or another input device is simple. The user does not have to look at the response device for selecting the response. |

In an embodiment one or more light sources are used to cause glare. Glare producing light source, which is visible to the eyes of the test subject, is situated in the vicinity of the display. In an embodiment the said light source is adjustable in intensity in order to cause glare to the person. Glare causes decreased performance in recognition of the symbol. In an embodiment a light source producing glare can be used as a fixation object when testing the visual field with a perimeter.

In an embodiment the spectral distribution of the light source used to produce glare is adjustable. In an embodiment the spectral distribution of the said light source used to produce glare is adjustable in the short wavelength end of the visible spectrum. This may be achieved e.g. by means of different color LEDs.

Spectrally adjustable glare lights are useful e.g. when assessing the glare sensitivity of a person towards glare from halogen or xenon lamps of approaching cars in a traffic situation or when determining usefulness of spectrally different absorbing eyeglasses, i.e. absorption lenses, relieving the symptoms of a person who has increased glare sensitivity.

In an embodiment the symbol size is automatically calibrated to the measurement distance. The distance may be provided by proximity sensors, so that the fluctuation of the examination distance caused by the subject looking at closer distance doesn't cause error in the measurement of the visual acuity.

DESCRIPTION OF SOME POSSIBLE EMBODIMENTS

In this text the examples mainly speak of assessing whether a person fulfills driver requirements for safe driving, but the medical device and method according to the invention may be used in a variety of situations, e.g. diagnosing disease, job selection, visual competence assessment, school or community screenings, military selection, and disability classifications.

One method for testing a patient with a stand-alone medical device in one-piece configuration comprises at least the following steps:
  testing visual field of the patient with a first testing device comprising a perimeter device;
  testing one or more second tests with a second testing device, the second tests selected from the group of:
    a) testing of visual acuity,
    b) testing of contrast sensitivity,
    c) testing of glare;
  controlling the use of the first and second testing devices with a user interface device.

The medical device being stand-alone means that in a normal use situation it is capable of functioning alone, save perhaps electric power connections. In an embodiment the device comprises rechargeable batteries, thereby also removing the need for electric power connections during normal use.

The medical device being of one-piece configuration means that in a normal use situation necessary parts needed for testing a patient are comprised in one single entity. Some parts are may be turnable, e.g. hinged together and it is naturally possible that some parts may be disconnectable from each other. In an embodiment the medical device is of one-piece configuration in normal use, but also when transported or stored without actually using it.

A typical first testing device comprises a perimeter surface, i.e. a perimeter device which is a medical diagnostic device for human visual field testing. The perimeter surface has a first side to be viewed by the patient during testing and second side not to be seen by the patient during testing. Also other tests, e.g. neuropsychological tests can be run on the perimeter surface. In an embodiment the first side of the perimeter surface has a curved shape, the concave surface arranged towards the first side of the perimeter surface, i.e. towards the patient being tested.

The perimeter should be large enough to be capable of measuring visual field size. Perimeters and their use is well known in the art and therefore not explained in detail here. The perimeter can be e.g. a standard automated perimeter or a multi-fixation perimeter.

Now it has now been found that unexpected advantages may be achieved if one or more second testing device is integrated in the same stand-alone device with the perimeter. In An embodiment the second testing device is selected from the group of:
  a visual acuity measurement device,
  a contrast sensitivity testing device,
  a glare testing device.

The second testing device is arranged to be viewed by the patient, i.e. it is visible to the first side of the perimeter surface during the test it performs. The second testing devices and second tests can include other tests too, e.g. neuropsychological tests. Glare testing means any type of glare tests. In an embodiment of the invention the glare testing comprises testing of one or more of the following types of glare: disability glare, discomfort glare, adaptation glare. Glare testing device is arranged capable of testing one or more of said types of glare. The above mentioned second testing devices and second tests, i.e. visual acuity measurement, a contrast sensitivity testing and a glare testing, are as such known to the art, therefore they are not explained in further detail here.

Further, a medical device may comprise a user interface device for controlling the use of the first and second testing devices. In an embodiment the user interface device is at least for a limited time useable and visible for the supervising person only, that is to the second side of the perimeter surface. When the device is a stand-alone, one-piece device, all tests can easily be controlled with one single user interface device.

It is possible that the tests on the first and second testing devices are performed without a computer in the medical device itself. But in an embodiment of the invention the medical device comprises a computer with memory and a computer program code to be run on the computer memory. The computer program would then be arranged to perform the tests on the first and/or second testing devices. The computers and computer programs and data connections needed are known in the art. Computer programs can be made to perform effective testing.

In an embodiment of the invention the medical device comprises a display unit for the one or more second testing devices. The display unit would comprise a display to be viewed by the patient during testing. The display unit is arranged to show elements of the second visual test to be tested on the display. The display unit thus works as stimulus and test symbol (i.e. optotype) presentation device for e.g. visual acuity, contrast sensitivity, glare tests. In an embodiment the computer program would control what is shown on the display. Electrical displays are very effective in showing elements in the tests mentioned above. The display of the display unit may be e.g. an LCD panel.

In an embodiment of the invention the user interface device comprises the display unit, which is also used as the second testing device.

In an embodiment of the invention the computer is situated in the device of the invention, e.g. in the display unit or inside the perimeter surface.

In an embodiment of the invention the user interface device for controlling the use of the first and second testing devices is in the display unit. The display unit may comprise mechanical buttons, switches or similar, but it is possible to arrange these control means into a touchscreen, which is an electronic visual display that the user can control through simple or multi-touch gestures by touching the screen with one or more fingers. The display of the display unit may be this touchscreen for controlling the use of the first and second testing devices. In an embodiment of the invention the same display functions as a touchscreen for controlling the use of the first and second testing devices and as a display showing elements of the second visual test to be tested for the patient. The display unit may be a tablet computer or another portable device such as a phone.

In an embodiment of the invention the display unit is arranged turnable between at least two positions, i.e. in the first and second position. In the first position the display can be viewed from the first side of the perimeter surface, i.e. by the patient to be tested. In the second position the display can be viewed from the second side of the perimeter surface, i.e. by the person supervising the test. The display unit may be kept in the second position e.g. when performing a test with the first testing device, i.e. with the perimeter surface. This way the person supervising the test may supervise and control the test with the display unit. When turned into the first position, the display can function as a display showing elements of the second visual test to be tested for the patient.

If the display unit is a portable device such as a tablet computer or a phone, the medical device may comprise one or more attaching points such as a holder or a bracket or a support where the display unit may be releaseably attached. E.g. one attaching point may be arranged on the first side of the perimeter surface or in such way that the display may be seen and used from the first side. Also one attaching point may be arranged on the second side of the perimeter surface or in such way that the display may be seen and used from the second side. An attaching point for the portable device may be such that the portable device can be attached to it in two positions: the display towards the first side or towards the second side.

An integrated and turnable display unit provides simplicity and cost-efficiency. The efficiency of the second tests is enhanced when the display is turned to the first side of the perimeter surface. That is because the display is then surrounded by the large perimeter surface, whereby the visual field of the person to be tested is kept free of disturbing visual objects which would interfere with the test stimuli presented on the display panel and disturb the concentration of the person.

In an embodiment of the invention the perimeter surface is arranged foldable between at least two positions, i.e. a use position and a transport position. In the use position the perimeter surface is arranged open and the first side of the perimeter surface may be viewed by the patient. In transport position the perimeter surface is folded so that at least a part of the first side of the perimeter surface is not viewable by the patient and more protected. Also, in transport position the perimeter surface takes less space and makes the device easier to transport or store between uses. If the display unit is a portable device, its transport position may be such, that when attached to its attaching point, the display is turned against the first or second side of the perimeter surface.

In an embodiment of the invention the display unit is arranged turnable into a transport position, where the display is arranged against the first side of the perimeter surface and not viewable by the patient. This protects the display and makes the device easier to transport or store between uses.

In further embodiments of the invention the medical device has a handle e.g. on the top of the perimeter surface for easy portability. In an embodiment a support leg, for allowing the device to be kept in a suitable position e.g. on a table, is arranged turnable on the device. The turnable support leg may assist in arranging the perimeter surface and/or display unit to be in a suitable position, e.g. perpendicular to the patient The support leg may also be arranged to be used as a carrying handle and for hanging the device e.g. on a wall.

In an embodiment of the invention the medical device comprises ambient light sensors arranged to detect lighting conditions around the device and arranged to monitor and/or adjust the performance of the first and/or second testing devices and the second tests. Ambient light sensors are well known as such. They are used to detect light or brightness in a similar way as the human eye. They are used wherever the settings of a system have to be adjusted to the ambient light conditions as perceived by humans. Ambient light sensors may be integrated in the perimeter, in the display unit or elsewhere in the device.

In an embodiment of the invention ambient light sensors are used to monitor the lighting behind the device in order to detect too bright areas, e.g. window, or too dark areas in the examination room which would disturb the visibility of the test stimuli which are presented by the device for the person.

In an embodiment of the invention ambient light sensors are used to monitor the ambient lighting of the room which illuminates the first surface of the perimeter surface in order to detect if the illumination in different parts of the surface of the device is uniform and adequate.

In an embodiment of the invention ambient light sensors are used to adjust the intensity i.e. luminance of the perimeter stimuli and fixation objects during the test based on the illumination of the perimeter surface so that the luminance contrast can be set at the desired level. Luminance contrast $C_W=(L_s-L_b)/L_b$; where $L_s$ is luminance of the stimulus and $L_b$ is the luminance of the background, i.e. the perimeter surface.

In an embodiment of the invention ambient light sensors are used to adjust the brightness i.e. luminance and contrast of the display of the display unit during the test according to the illumination of the perimeter surface.

In an embodiment of the invention ambient light sensors are used to adjust the glare light intensity according to the illumination of the perimeter surface.

In an embodiment of the invention the medical device comprises proximity sensors arranged to detect the position of the patient and arranged to monitor and/or adjust the performance of the first and/or second testing devices. Proximity sensors may be integrated in the perimeter, in the display unit or elsewhere in the device.

In some embodiments of the invention the optotype size showed to the patient on the display unit when performing visual acuity measurement, contrast sensitivity testing or glare testing is automatically varied depending on the distance of the patient measured by the proximity sensors. Normally, the further from the device the patient is, the larger the optotype size showed to the patient.

In some embodiments of the invention the ambient light and proximity sensors are used for validating the measurement conditions during testing. If e.g. the patient moves into an invalid position the device may give a warning or guidance to the patient or the test operator/supervisor to correct the patient's position.

In some embodiments of the invention the perimeter measurement grid, i.e. visual field test points produced e.g. by light matrixes on the perimeter surface, are automatically adjusted according to the patient head position i.e. distance from the perimeter surface.

In an embodiment of the invention the medical device comprises one or more glare lights or glare sensitivity test lights to be lighted towards the patient during testing of glare sensitivity or other glare tests. The glare lights may be integrated in the perimeter, in the display unit or elsewhere in the device. In an embodiment of the invention the glare light spectrum is arranged to be varied, e.g. to test sensitivity differences to different light sources, such as halogen or xenon headlamps. The glare light spectrum can be varied e.g. by producing the glare light with lamps e.g. LEDs of different colors and by varying their effect.

In an embodiment of the invention the first testing device comprises at least one light matrix, such as a LED (light-emitting diode) matrix or an OLED (organic light-emitting diode) matrix or an LCD (liquid-crystal display) matrix. The light matrix or matrixes are arranged capable of displaying perimeter stimulus and/or fixation objects to the first side of the perimeter surface, i.e. to be seen by the patient. Perimeter stimulus and/or fixation objects are figures or shapes that can be discriminated from each other by the patient during testing. Lights on the perimeter surface are known as such, but light matrixes enable new kind of effective tests, as the light matrixes (such as implemented with LEDS) can provide more light output and therefore the dynamic range will be higher than with commercially available large display panels. Curved shape of the perimeter surface built with separate display matrix units offers the possibility extend visual field measurements to over 90 degrees from fixation point, which is not possible with perimeter using only one or two flat display panels.

In an embodiment of the invention the first side of the perimeter surface is covered with a translucent layer, made e.g. of suitable plastic material. The layer is arranged to hide the light matrix from the patient when the light matrix is not lighted. But when a light in the light matrix is lighted, the layer is arranged to let light through it in order to show the position of the perimeter stimulus and/or fixation objects to the patient. When the perimeter translucent surface is matt, not glossy, there will be an advantage over LCD or OLED displays that the perimeter testing can be executed under normal room lighting without fear of reflections on display disturbing the measurement results.

In an embodiment of the invention the perimeter surface has light sources, such as light openings or additional LEDs or other light sources towards its second side. These lights or openings are situated at the positions where the lights, e.g. LEDs of the light matrix are situated on the first side of the perimeter surface. This way a doctor or other person supervising the test from the second side of the perimeter surface can simultaneously see both where the patient is looking, and also the position of the lighted light, i.e. a fixation object or visual stimulus.

In an embodiment of the invention the medical device, e.g. the perimeter surface, incorporates two or more loudspeakers. Loudspeakers may be used e.g. for testing sensory integration of vision and visual oculomotor function where auditory system can be assessed using localizing sound stimuli from the loudspeakers of the device which guide the gaze to find the tiny fixation objects on the perimeter surface. Loudspeakers may also be used when assessing spatial hearing and sensory integration (i.e. spatial hearing & spatial vision). Loudspeakers allow auditory guidance of the saccades of the test subject in perimeter to locate a fixation object which is detectable only by foveal vision. The loudspeakers may be situated e.g. on the first surface of the perimeter surface, hidden behind the translucent layer.

In an embodiment of the invention the medical device comprises at least one attachment point for a camera or eye-tracker for recording the eye movements of the patient during testing. The attachment point may be situated e.g. on an edge of the perimeter surface.

The display of the display unit can be used for many kinds of neuropsychological tests, e.g. memory guided saccade, anti-saccade or the Trailmaker test. The perimeter surface can also be used for memory guided saccade and anti-saccade testing.

One possible use of the device is so called armed fixation point perimetry. There a standard automated perimeter (SAP) with fixation control is built so that only when the fixation object (e.g. "O") changes its form to "report" or "armed" figure (e.g. "+") the patient may report if he/she saw a stimulus. When the fixation object changes to "trap" or "disarmed" figure (e.g. "−") the patient must not report even if he/she saw a stimulus. The reporting may be done e.g. by pushing a relevant button. This ensures the patient must look at the fixation object with foveal vision at all times.

The fixation object may in addition move slowly or with small steps on the perimeter surface, in order to help the patient to keep fixation to the fixation object, and to allow testing more test points with a relatively small perimeter surface.

A multi-fixation perimeter can also be implemented as a First Pulse Perimeter (FPP) so that there will be multiple supra-threshold stimuli flashed to the patient, of which one will be shown earlier, e.g. 20 ms to 500 ms earlier, and the visual search task is to recognize which stimulus was presented earlier (the correct visual cue will be found under this). This kind of perimeter will measure the magno-cellular routes of the visual system, potentially useful for, e.g. glaucoma.

One of the advantages of some embodiments is how ambulatory use, i.e. portability of the device is made possible, e.g.: the device is of one-piece configuration; parts of the device e.g. perimeter panel, display unit, support leg, can be made foldable to reduce space needed and to protect the device; the device can be battery operated; the device is easily made light-weight (e.g. less than 5 kg); the support leg may form a handle for hanging on the wall for storage or for easy carrying of the device.

One advantage of some embodiments is that the automatic monitoring of the testing environment makes it possible to control for all important factors which have an effect on the measurement results made with the device, e.g.: the accuracy of the results are better than before; automatic operation of the testing procedure becomes possible; the device can notify the test supervisor or operator if the test situation is outside the limits of reliable operation and suggest actions to correct them; the test supervisor or operator doesn't have to be an expert in vision testing because the device takes care of possible sources of errors caused by inconsistent environment.

One advantage of some embodiments is that combining different tests and devices together gives unexpected synergy, e.g. the same proximity sensors and ambient light sensors can be used with tests with the perimeters surface and with the second testing devices, e.g. on the display unit. In other words, because the display unit can be turned to the first side of the perimeter surface the proximity sensors and ambient light meters for perimeter tests can be used in the tests for the visual acuity, contrast sensitivity and glare.

One advantage of some embodiments is that the testing of visual acuity, testing of contrast sensitivity and testing of glare, can be made automatic. In other words, the test subject replies to visual questions (i.e. optotypes) using a remote controller or pressing buttons or touch screen on the device itself. Many existing products only show visual questions but the test operator/supervisor must manually record the answers of the patient, decide whether the answer is right or wrong, step to next optotype in the algorithm and finally write down the results.

The applicants own patent application PCT/FI2013/050266 can be seen for more examples and details on the tests mentioned in this text. The application PCT/FI2013/050266, especially its text and especially the examples are hereby incorporated herein by reference.

BRIEF DESCRIPTION OF THE FIGURES

The invention is described in more detail below with reference to the enclosed schematic drawing, in which.

DETAILED DESCRIPTION OF THE EXAMPLES OF THE FIGURES

Figure 1:
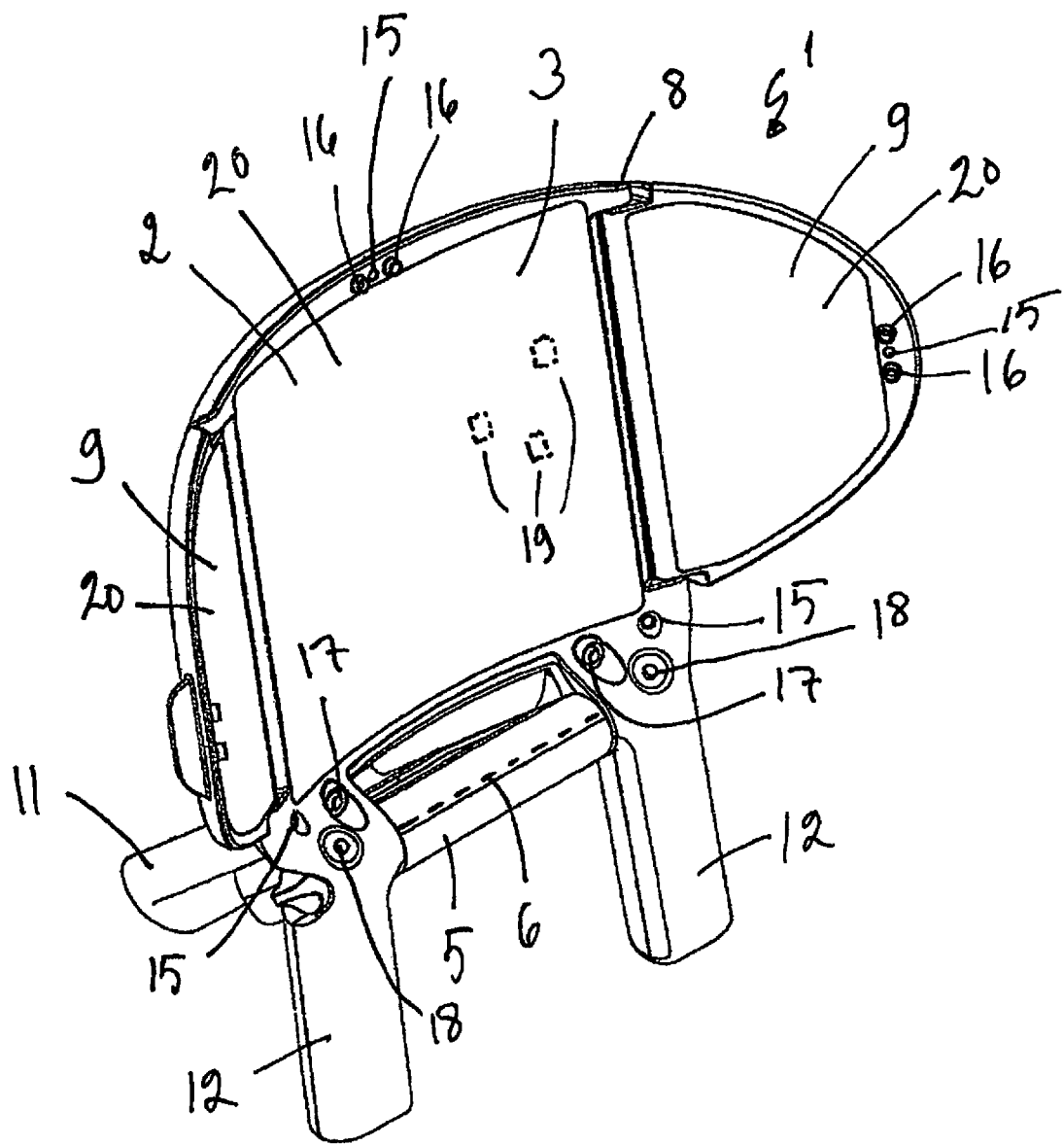
FIG. 1 shows a medical device according to the invention from the first side of the perimeter surface in a first situation.
Figure 2:
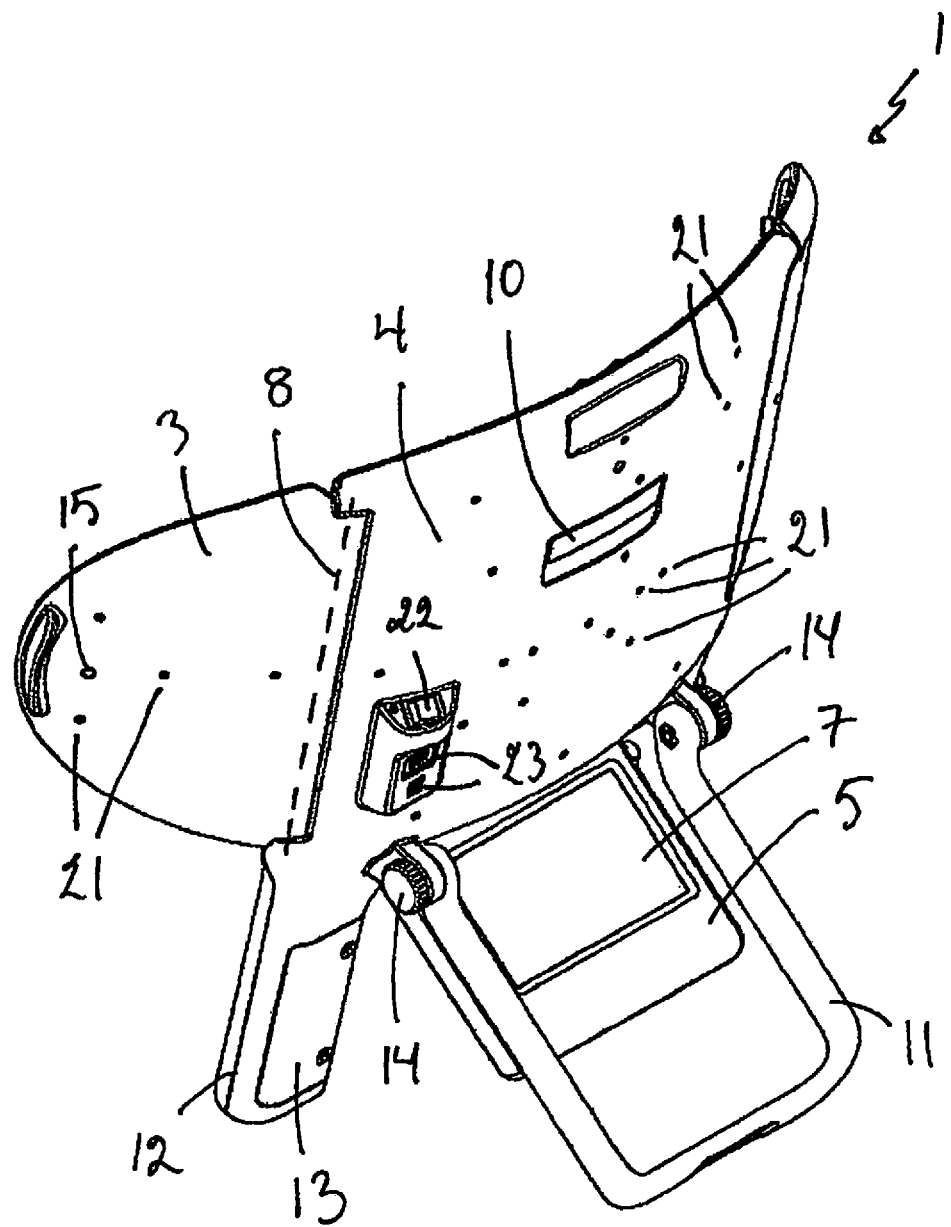
FIG. 2 shows the medical device of FIG. 1 from the second side of the perimeter surface.
Figure 3:
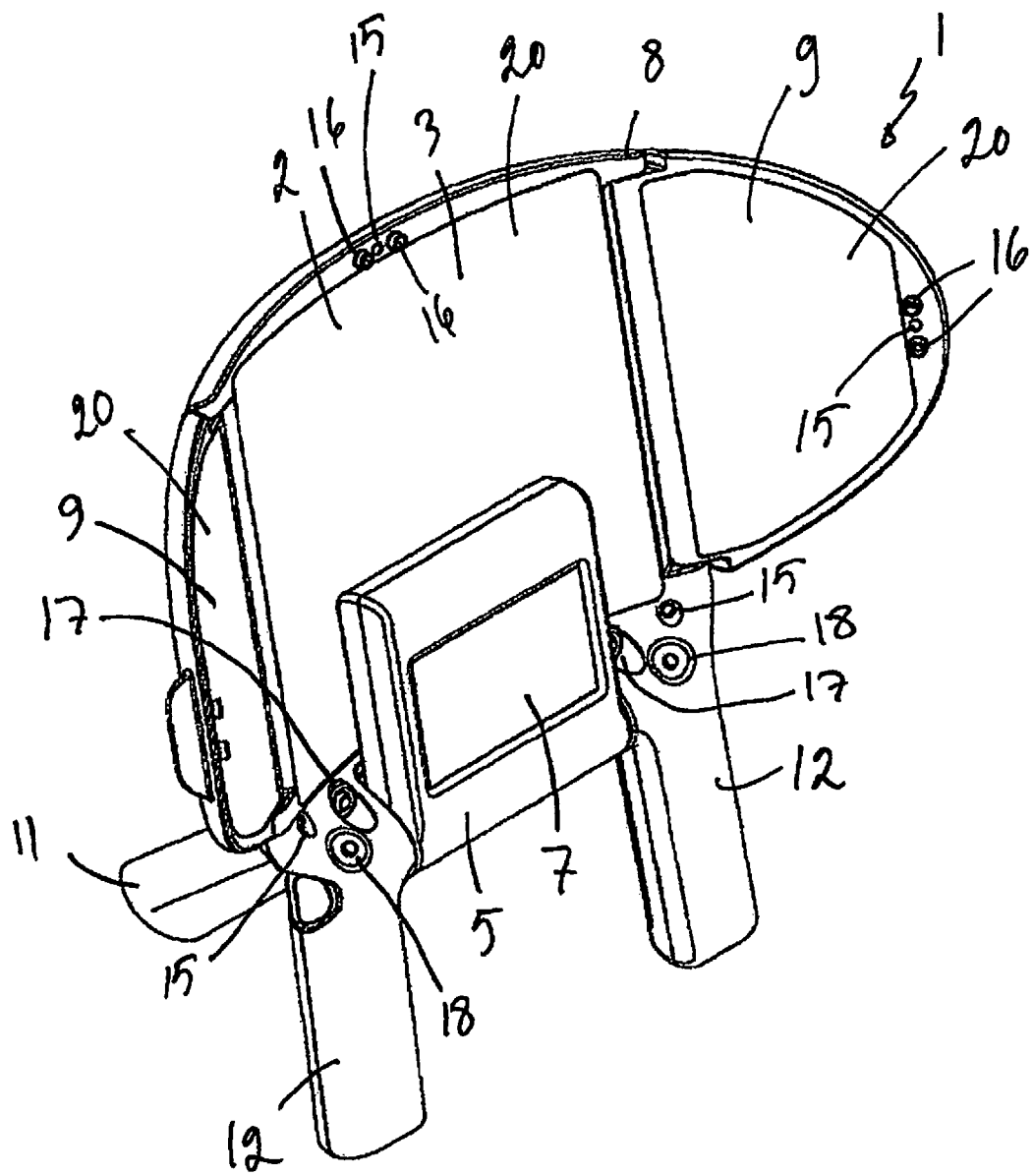
FIG. 3 shows a medical device according to the invention from the first side of the perimeter surface in a first second situation.
Figure 4:
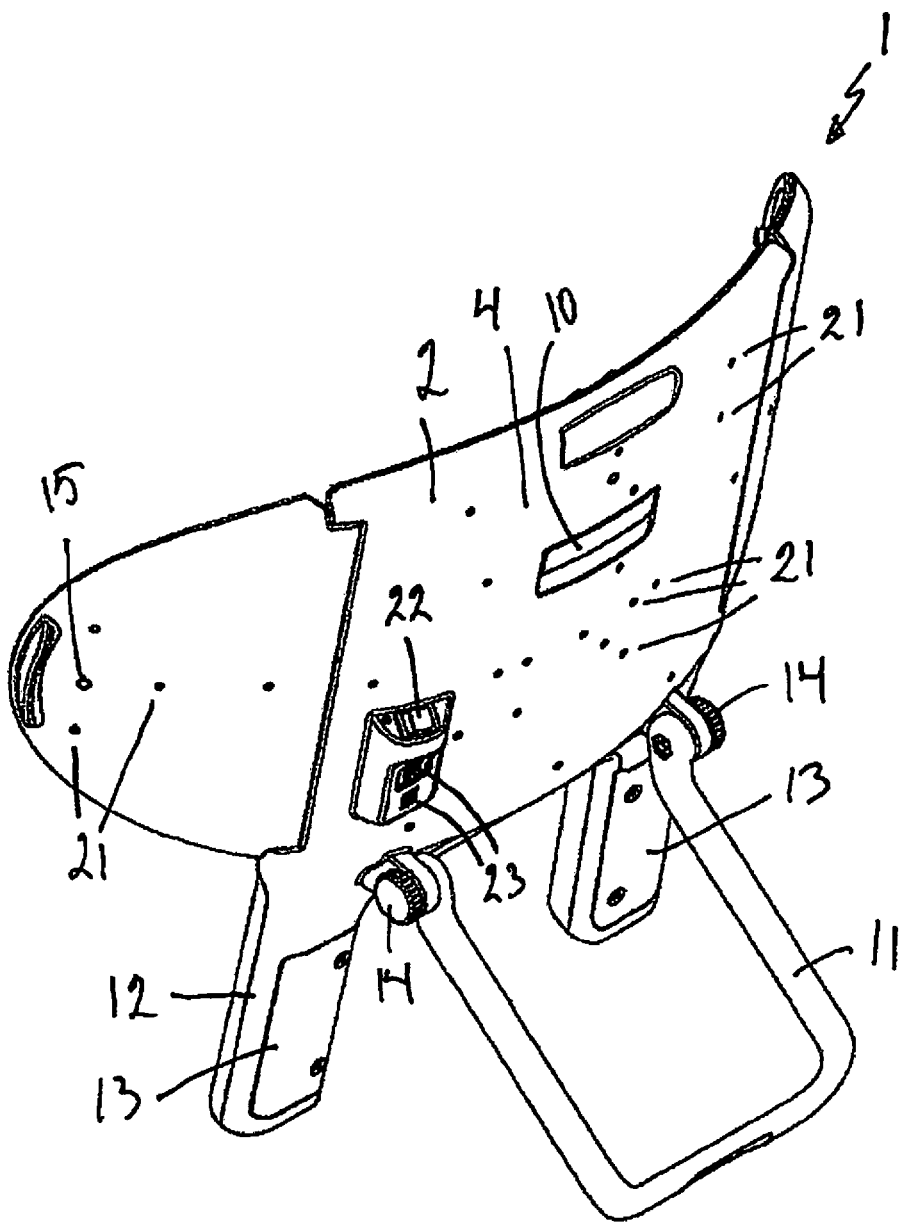
FIG. 4 shows the medical device of FIG. 3 from the second side of the perimeter surface.

For the sake of clarity, the same reference numbers are used for corresponding parts in different embodiments.

FIGS. 1 to 6 show a stand-alone medical device 1 for testing a patient according to the invention. The device 1 comprises a first testing device, i.e. a perimeter surface 2. The perimeter surface has a first side 3 to be viewed by the patient during testing and second side 4 not to be seen by the patient during testing. A display unit 5 is arranged turnable with hinge 6 below the perimeter surface. The display unit comprises a touchscreen display 7, which functions both as a user interface device and as a display to be viewed by the patient during testing of so called second tests. A computer controlling the use of the medical device is integrated inside the display unit 5 or the perimeter surface 2. The second tests, which are at least partly shown on the display 7, may comprise e.g. visual acuity measurement, contrast sensitivity testing or glare testing.

The display unit 5 is arranged turnable between at least two positions, i.e. the first position (see FIG. 3) and the second position (see FIG. 1). For transport and storage, it is possible that the display unit 5 is further turned into a transport position (see FIG. 5), but this may be the same position as e.g. the first position. In the first position the display 7 can be viewed from the first side 3 of the perimeter surface, i.e. by the patient to be tested. In the second position the display 7 can be viewed from the second side 4 of the perimeter surface, e.g. by the person supervising the test. The display unit 5 may be kept in the second position e.g. when performing a test with the first testing device, i.e. with the perimeter surface 2. This way the person supervising the test may supervise and control the test with the user interface in the display unit 5.

Figure 5:
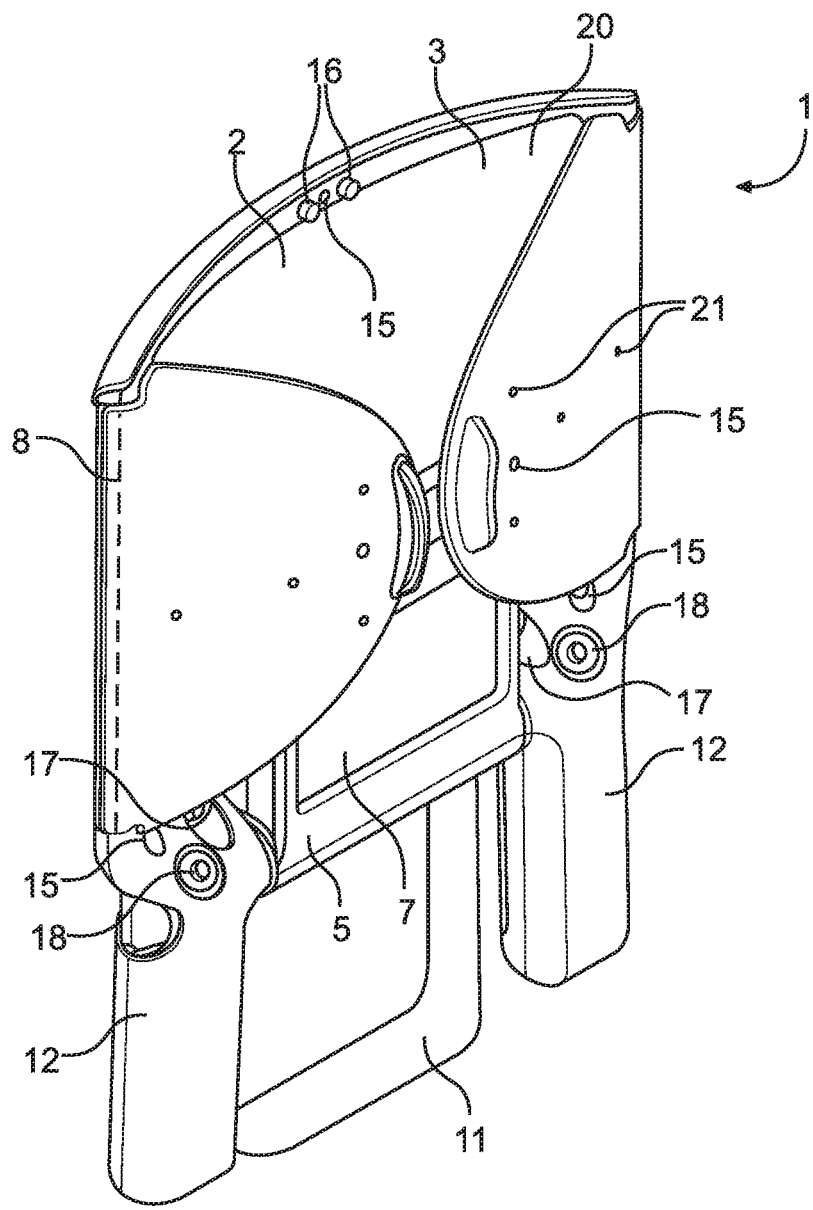
FIG. 5 shows a medical device according to the invention from the first side of the perimeter surface in a third situation.
Figure 6:
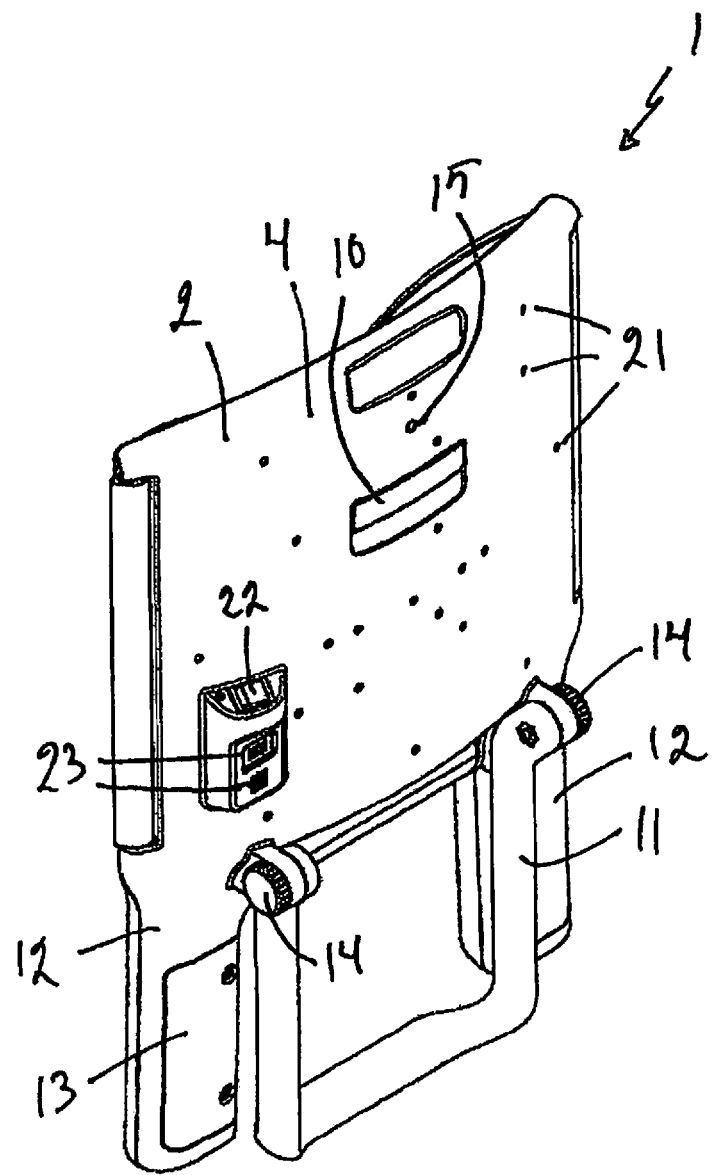
FIG. 6 shows the medical device of FIG. 5 from the second side of the perimeter surface.

The perimeter surface 2 is arranged foldable around hinges 8 between at least two positions, i.e. a use position (FIG. 1) and a transport position (FIG. 5). In the use position the perimeter surface 2 is arranged open and the first side 3 of the perimeter surface 2 may be viewed by the patient. In transport position the perimeter surface 3 is folded so that side parts 9 of the first side 3 of the perimeter surface are not viewable by the patient.

A handle 10 is situated near the top of the second side 4 of the perimeter surface 2. A turnable support leg 11 allows the device to be kept in a suitable position e.g. on a table. The support leg 11 may be turned between at least two positions, the use position (FIG. 1) and the transport position (FIG. 5). Batteries are situated in stationary legs 12, behind lids 13. The movement of the turnable support leg 11 may be controlled with clamping screws 14. Ambient light sensors 15 are arranged in the device to detect lighting conditions around the device 1 and to monitor and/or adjust the performance of the first and/or second testing devices 2, 3.

Proximity sensors 16 are arranged in the device to detect the position of the patient. Glare lights 17 to be lighted towards the patient during testing of glare are situated near the display unit 5. Buttons 18 may be used by the patient in some tests, e.g. to indicate if a visual stimulus was seen.

The first testing device comprises at least one light matrix 19, such as a LED matrix or an OLED matrix or an LCD matrix, capable of displaying perimeter stimulus and/or fixation objects at least to the first side of the perimeter surface. The positions 19 of the matrix lights shown in FIG. 1 are only exemplary, the positions of the lights in the light matrix may be selected in various ways. The first side 3 of the perimeter surface 2 is covered with a translucent layer 20, which hides the light matrix 19 from the patient when the light matrix is not lighted. But when a light in the light matrix is lighted, the light is seen through the translucent layer 20.

The perimeter surface 2 comprises several small light openings 21 towards its second side 4. The openings 21 are situated at the positions where the lights, e.g. LEDs of the light matrix 19 are situated on the first side 3 of the perimeter surface 2. This way the person supervising the test from the second side 4 of the perimeter surface 2 can see where the fixation object or visual stimulus is lighted.

A power on/off-switch 22 and I/O-sockets 23 are situated on the second side 4 of the perimeter surface 2.

Figure 7:
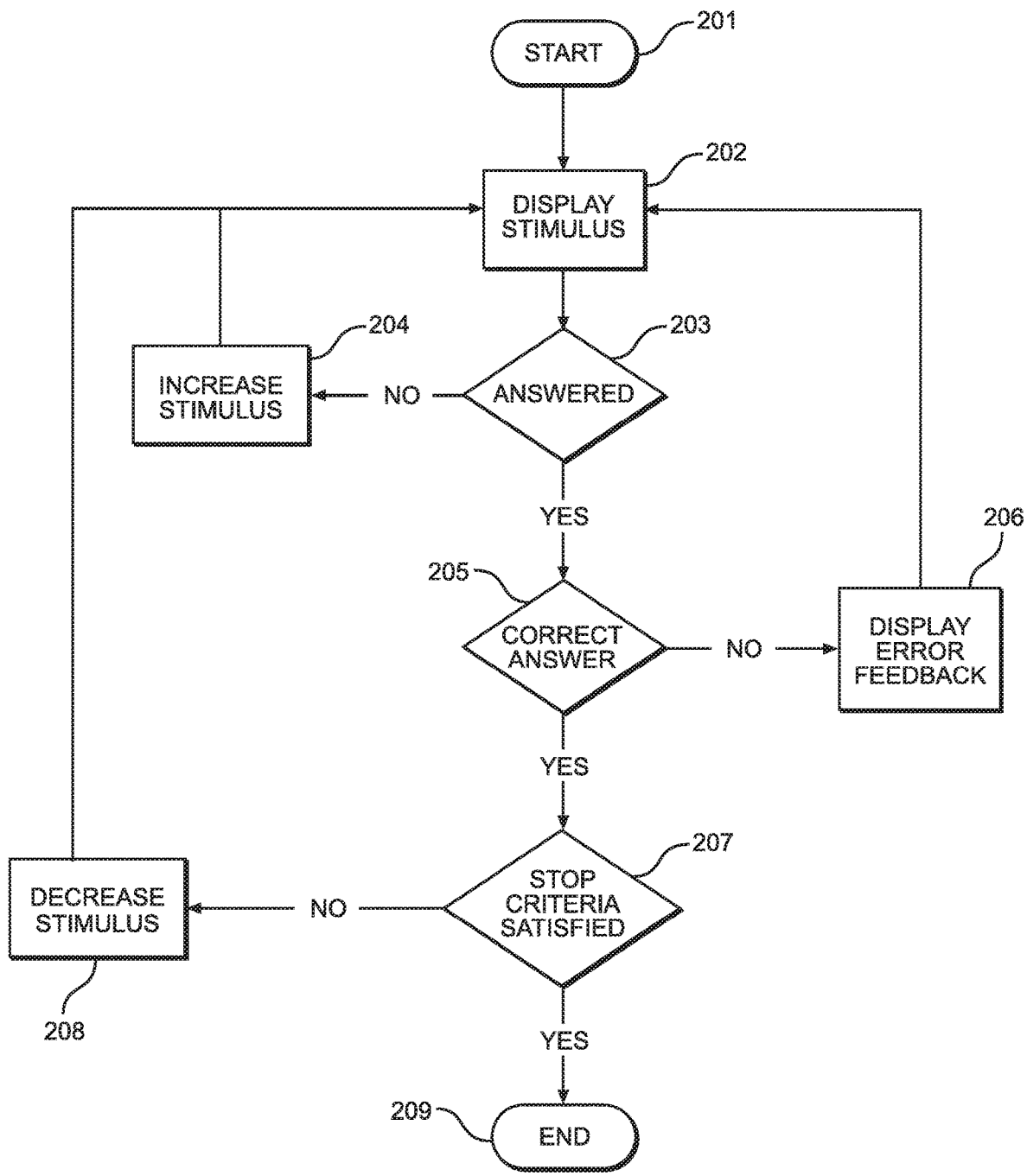
FIG. 7 shows a flow chart of a method according to the invention.

FIG. 7 shows a flow chart of one possible method and computer program of the invention. In step 201 the method is started. In step 202 a symbol with a distinctive visual appearance and with a stimulus level is displayed to a display. In step 203 a response device is monitored. If a response is not given in a response time-limit the stimulus level of the symbol is increased by a predetermined step in step 204 and the program is returned to step 202. On the other hand, if a response is given in the response time-limit the program continues to step 205. In step 205 the response from step 203 is compared to the symbol displayed in step 202. If the response does not correspond to the symbol displayed an error feedback is displayed in step 206 and the program is returned to 202 for displaying of a new symbol with the same stimulus level as with the previous symbol. On the other hand, if in step 205 the response from step 203 corresponds to the symbol displayed in step 202 the program proceeds to step 207 for determining if stop criteria for the test is satisfied. If stop criteria for the test is not satisfied, the stimulus level is decreased by a predetermined step in step 208 and the program is returned to step 202. On the other hand, if in step 207 stop criteria is satisfied, program terminates in step 209.

Figure 8:
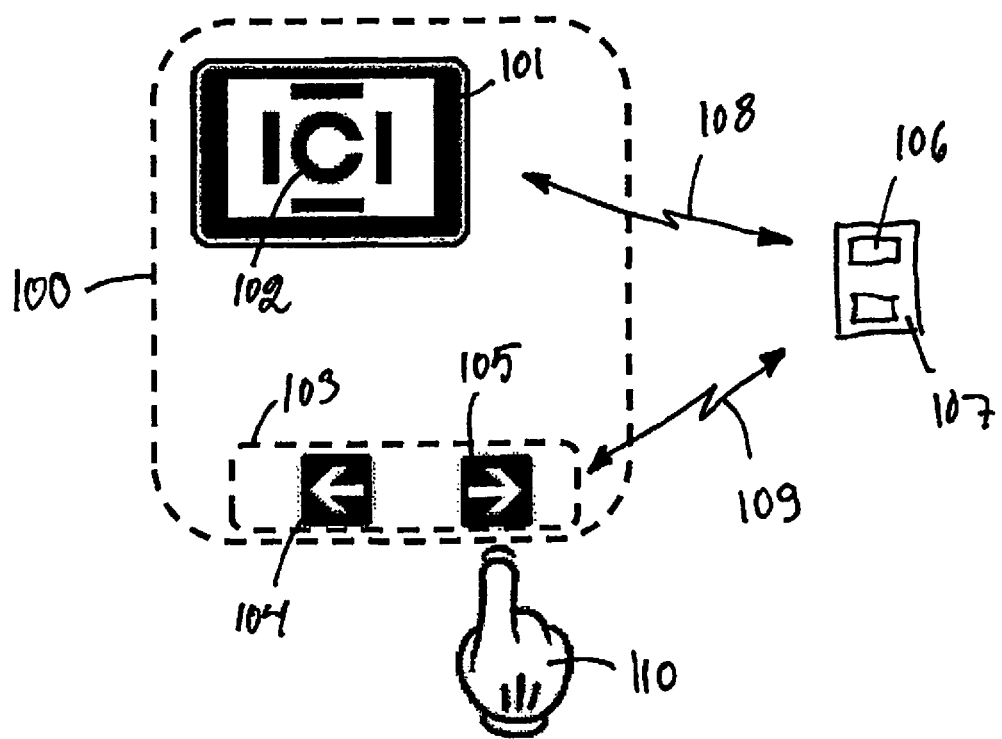
FIG. 8 shows an apparatus according to the invention.

FIG. 8 shows an apparatus for testing and determining a threshold value in visual acuity, contrast sensitivity, color vision deficiency or glare sensitivity. The apparatus 100 comprises a display 101 for displaying a symbol 102 and a response device 103 with two choice actuators, i.e. buttons 104 and 105. Each button represents a possible visual appearance of the symbol 102, in this case orientation of the symbol either to the left or to the right.

In FIG. 8 a patient or test subject 110 watches the display 101, such as a tablet computer screen. When he/she identifies in which way the Landolt-C symbol 102 is oriented, he/she makes a decision to press the button which corresponds to that orientation. In the example the symbol 102 is oriented to the right and the test subject 106 is about to press the corresponding button 105 with an arrow to the right.

A computer program runs on the memory 106 of computer 107. The program sends instructions to the display 101 via electronic data communication link 108 on which symbols 102 to display. The computer 107 also receives, via another data communication link 109, knowledge from response device 103, such as a mobile phone application, of which button 104 or 105 is pressed and at which time-point.

The button 105 in FIG. 8 is the correct one and if it is pressed before time-out, a correct response is recorded in the memory 106 of the computer 107 of the apparatus.

Figure 9A:
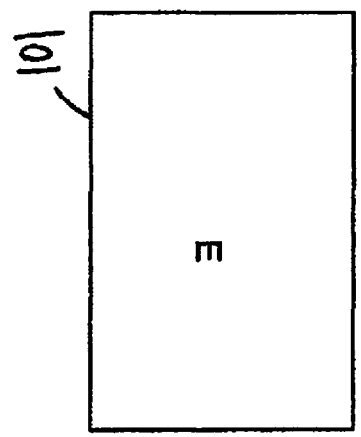
FIGS. 9a to 9f show some symbols, such as an optotypes, patterns or tasks according to the invention.

FIGS. 9*a* to 9*f* show some examples of symbols, such as an optotypes, patterns or tasks according to the invention displayed on a display 101. FIG. 9*a* shows a traditional tumbling E, and the task for the test subject could be e.g. "Which direction are the fingers of the 'E' pointing to?" The right answer would be: "Left".

Figure 9B:
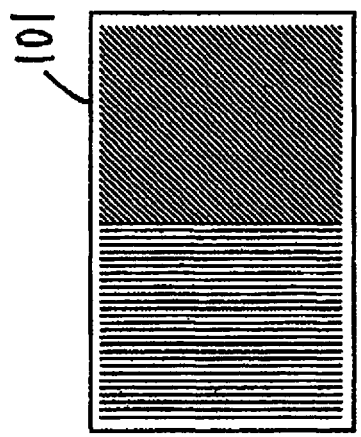

FIG. 9*b* shows two different patterns, vertical and diagonal stripes, on different sides of the display 101. The task for the test subject could be e.g. "On which side (left or right) the stripes are vertical?" The right answer would be: "Left".

Figure 9C:
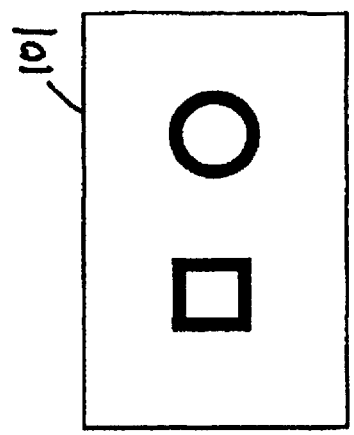

FIG. 9*c* shows two different symbols, a square and a circle, on different sides of the display 101. The task for the test subject could be e.g. "On which side (left or right) there is a square?" The right answer would be: "Left".

Figure 9D:
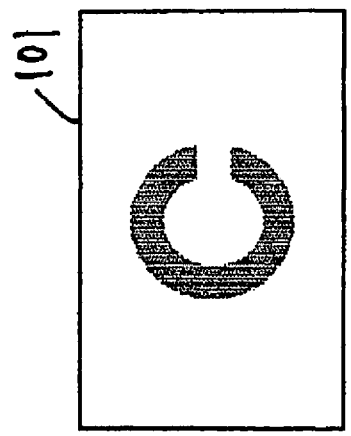

FIG. 9*d* shows a gray Landolt C on a white background of display 101. The task for the test subject could be e.g. "Which direction is the gap of the 'C' pointing to?" The right answer would be: "Right".

Figure 9E:
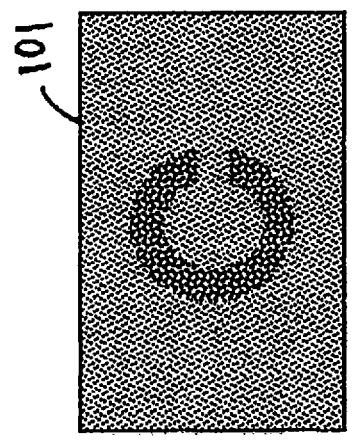

FIG. 9*e* shows a gray Landolt C on a lighter grey background of display 101. The task for the test subject could be e.g. "Which direction is the gap of the 'C' pointing to?" The right answer would be: "Right". The background and the symbol on the foreground could also be of different colors.

Figure 9F:
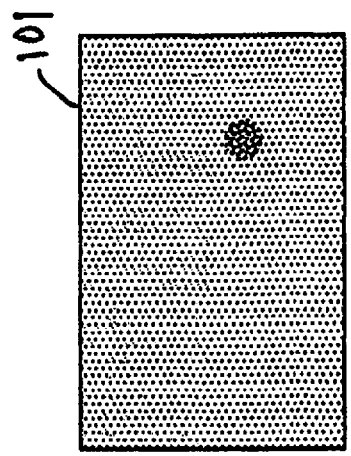

FIG. 9*f* shows a gray dot on a lighter grey background of display 101. The task for the test subject could be e.g. "On which side (left or right) there is a dot?" The right answer would be: "Right".

The figures show only a few preferred embodiments. Facts of secondary importance with regards to the main idea of the invention, facts known as such or evident for a person skilled in the art, such as power sources or support structures possibly required by the invention, are not necessarily separately shown in the figures. It is apparent to a person skilled in the art that the invention is not limited exclusively to the examples described above, but that the invention can vary within the scope of the claims presented below. The dependent claims present some possible embodiments of the invention, and they are not to be considered to restrict the scope of protection of the invention as such.

The invention claimed is:

1. Method for testing and determining a threshold value in psychometric testing in field of ophthalmology, neuro-ophthalmology and visual neuropsychology, the method comprising at least the following steps:
   a) displaying a symbol (102) with a distinctive visual appearance and with a stimulus level to a display (101) at a stimulus time-point, the symbol having been selected from a group of possible symbols,
   b) monitoring if a response is given on a response device (103) with multiple choices (104, 105), each choice representing a possible visual appearance or location of the symbol, and
   b1) if a response is not given in a response time-limit from the stimulus time-point, increasing the stimulus level of the symbol by a predetermined step and returning to step a), or
   b2) if a response is given in the response time-limit from the stimulus time-point, comparing the response to symbol (102) displayed in step a), and
   c1) if the response does not correspond to the symbol displayed in step a), producing an error feedback and returning to step a) to display a new symbol having the same stimulus level as the previous symbol, d1) if stop criteria for the test is not satisfied, decreasing the stimulus level by a predetermined step and returning to step a), or d2) if stop criteria for the test is satisfied, ending the test.

2. Method according to claim 1, wherein said response time-limit is more than 0.5 seconds but less than 3 seconds.

3. Method according to claim 1, wherein said group of possible symbols comprises only two possible symbols.

4. Method according to claim 1, wherein said stimulus level of the symbol is the size of the symbol.

5. Method according to claim 1, wherein said stimulus level of the symbol is the contrast level of the symbol on the display.

6. Method according to claim 1, wherein if a response is not given in a response time-limit and the previous response corresponded to the displayed symbol, or if the response corresponds to the symbol displayed and the previous response was not given in a response time-limit, then the predetermined step by which the stimulus level of the symbol is changed is decreased from its previous value.

7. Method according to claim 1, wherein, if for a number of times in a row, a response is not given in the response time-limit from the stimulus time-point, or the response corresponds to the symbol displayed in step a), then the predetermined amount by which the stimulus level of the symbols are changed is increased.

8. The method of claim 1, wherein said error feedback is a member of the group consisting of a visual message, an audible error sound and a vibration message.

\* \* \* \* \*